United States Patent
Van Kesteren et al.

(10) Patent No.: US 8,040,516 B2
(45) Date of Patent: Oct. 18, 2011

(54) OSCILLATOR ELEMENT FOR PHOTO ACOUSTIC DETECTOR

(75) Inventors: Hans Willem Van Kesteren, Eindhoven (NL); Ivon Franciscus Helwegen, Herten (NL); Jeroen Kalkman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 263 days.

(21) Appl. No.: 12/513,521

(22) PCT Filed: Nov. 5, 2007

(86) PCT No.: PCT/IB2007/054472
§ 371 (c)(1),
(2), (4) Date: May 5, 2009

(87) PCT Pub. No.: WO2008/056312
PCT Pub. Date: May 15, 2008

(65) Prior Publication Data
US 2010/0045990 A1 Feb. 25, 2010

(30) Foreign Application Priority Data
Nov. 10, 2006 (EP) .................................. 06123826

(51) Int. Cl.
*G01N 21/00* (2006.01)
*G01N 21/17* (2006.01)
(52) U.S. Cl. .................... 356/432; 356/437; 73/24.02
(58) Field of Classification Search ............. 356/432, 356/437; 250/234, 225; 73/24.02, 504.16, 73/504.14, 504.12, 504.04, 1.82
See application file for complete search history.

(56) References Cited

U.S. PATENT DOCUMENTS

| | | | |
|---|---|---|---|
| 4,529,319 A | | 7/1985 | Muller |
| 5,212,985 A | * | 5/1993 | Takenaka et al. ........... 73/504.12 |
| 5,742,377 A | * | 4/1998 | Minne et al. .................... 355/71 |
| 6,094,971 A | * | 8/2000 | Edwards et al. ................. 73/105 |
| 6,182,508 B1 | * | 2/2001 | Takeuchi et al. ................ 73/493 |
| 6,378,368 B1 | * | 4/2002 | Iwata et al. ................ 73/504.14 |
| 6,415,643 B2 | * | 7/2002 | Watarai .......................... 73/1.82 |
| 6,523,410 B2 | * | 2/2003 | Matsubara et al. ......... 73/504.16 |
| 6,595,054 B2 | * | 7/2003 | Paros et al. ................ 73/504.04 |

(Continued)

FOREIGN PATENT DOCUMENTS

| DE | 3832906 A1 | 4/1989 |
|---|---|---|
| DE | 19911325 C1 | 7/2000 |

(Continued)

OTHER PUBLICATIONS

Kosterev et al: "Applications of Quartz Tuning Forks in Spectroscopic Gas Sensing"; Review of Scientific Instruments, American Institute of Physics, vol. 76, No. 4, pp. 043105-1-043105-9.

*Primary Examiner* — Sang Nguyen (57) ABSTRACT

An oscillator element is provided, e.g., for use in a photo acoustic detector for detecting a concentration of a sample in a sample mixture using a light beam for excitation of molecules of the sample in proximity of an excitation area of the oscillator element. The oscillator element includes piezoelectric material for generating a voltage when mechanically distorted. Electrodes at least partially cover a surface of the oscillator element for detecting the generated voltage. The excitation area is arranged in such a way that heating of the electrodes in the excitation area by the light beam is avoided.

11 Claims, 6 Drawing Sheets

U.S. PATENT DOCUMENTS

| | | | |
|---|---|---|---|
| 6,835,926 B2 * | 12/2004 | Weitekamp et al. | 250/234 |
| 6,930,440 B2 * | 8/2005 | Chiba et al. | 310/370 |
| 7,245,380 B2 * | 7/2007 | Kosterev | 356/437 |
| 7,605,922 B2 * | 10/2009 | Willing et al. | 356/437 |
| 2005/0117155 A1 | 6/2005 | Kosterev | |
| 2009/0229345 A1 * | 9/2009 | Van Kesteren | 73/24.02 |

FOREIGN PATENT DOCUMENTS

| | | |
|---|---|---|
| DE | 10321806 A1 | 12/2004 |
| EP | 0142481 A2 | 5/1985 |
| WO | 03104767 A2 | 12/2003 |
| WO | 2006072867 A1 | 7/2006 |
| WO | 2008056307 A1 | 5/2008 |

* cited by examiner

OSCILLATOR ELEMENT FOR PHOTO ACOUSTIC DETECTOR

CROSS REFERENCE TO RELATED APPLICATION

This application claims the benefit of EP provisional application s/n 06123826.7, filed Nov. 10, 2006, which is incorporated herein by reference. A related application is PCT IB2007/054472, "Photo Acoustic Detector with Improved Signal Processing," filed Nov. 2, 2007, published as WO 2008/056307.

TECHNICAL FIELD OF THE INVENTION

The invention relates to an oscillator element for use in a photo acoustic detector for detecting a concentration of a sample in a sample mixture, the photo acoustic detector using a light beam for excitation of molecules of the sample in proximity of an excitation area of the oscillator element, the excitation resulting in resonance of the oscillator element, the oscillator element comprising piezoelectric material for generating a voltage when mechanically distorted and electrodes, at least partially covering a surface of the oscillator element for registering the generated voltage.

The invention further relates to a photo acoustic detector comprising such an oscillator element.

BACKGROUND OF THE INVENTION

Such an oscillator element is also used in the photo acoustic trace gas detector described in the United States patent application, published as US 2005/0117155. The photo acoustic trace gas detector uses a laser beam for exciting molecules of a trace gas in a gas mixture. The excitation of the trace gas molecules results in an increased temperature and pressure. The laser beam is wavelength or amplitude modulated for generating pressure variations in the gas mixture. In the photo acoustic trace gas detector according to US 2005/0117155, a quartz tuning fork detects the pressure variations. After amplification by a pre-amplifier, a lock-in amplifier mixes the tuning fork signal with a reference signal for acquiring an output signal. The use of the quartz tuning fork for the detection of the pressure variations allows for a relatively compact photo acoustic trace gas detector.

An important application of photo acoustic trace gas detectors is breath testing. Breath testing is a promising area of medical technology. Breath tests are non-invasive, user friendly and low cost. Prime examples of breath testing are monitoring of asthma, alcohol breath testing and detection of stomach disorders and acute organ rejection. First clinical trials show possible applications in the pre-screening of breast and lung cancer. These volatile biomarkers have typical concentrations in the parts per billion (ppb) range. Nitric oxide (NO) is one of the most important trace gases in the human breath, and elevated concentrations of NO can be found in asthmatic patients. Currently, exhaled NO levels at ppb concentrations can only be measured using expensive and bulky equipment based on chemiluminescence or optical absorption spectroscopy. A compact, low-cost NO sensor forms an interesting device that can be used to diagnose and monitor airway inflammation and can be used at the doctor's office and for medication control at home.

For detecting NO in the exhaled breath, an approach has been chosen where NO is chemically converted into $NO_2$ which is subsequently detected with a photo acoustic sensor incorporating a blue semiconductor laser. $NO_2$ has a broad absorption spectrum in the blue wavelength range, and consequently wavelength modulation is not the preferred modulation method for detecting $NO_2$. Unfortunately, amplitude modulation of the laser power leads to large background signals that easily dominate the small $NO_2$ related photo acoustic signals. It is a problem of the photo acoustic trace gas detector according to US 2005/0117155 that the accuracy of the measurements is not sufficient.

SUMMARY OF THE INVENTION

It is an object of the invention to provide an oscillator element according to the opening paragraph, which oscillator element improves the accuracy of state of the art photo acoustic detectors.

According to a first aspect of the invention, this object is achieved by arranging the excitation area in such a way that heating of the electrodes in the excitation area by the light beam is avoided.

The invention is based on the insight that the detector signals of the prior art photo acoustic detectors are adversely affected by strong direct excitation of the tuning fork pickup element which makes detection of the small photo acoustic signals difficult. In photo acoustic detection, the light beam is focused at the sample mixture, very close to the oscillator element to enable detection of the pressure variations by the oscillator element. Due to scattering of light, minor alignment inaccuracies and the width of the intensity distribution of the laser beam, the laser beam does not only excite sample molecules, but also directly parts of the oscillator element, leading to heating and the generation of a background signal. Throughout this text, the area in the proximity of the sample molecules exciting light spot, which area is also heated by the laser beam when the photo acoustic detector is in use, is called the excitation area. The heating of the excitation area results in expansion and mechanical distortion of the oscillator element, which leads to a voltage change, which is picked up via the electrodes. By arranging the excitation area in such a way that heating of the oscillator element by a light beam hitting the excitation area is avoided, the accuracy of the sample concentration detection is improved.

In a preferred embodiment of the oscillator element according to the invention, the electrodes do not cover the surface of the oscillator element in the excitation area. The direct excitation of the oscillator element is caused by absorption of the light in the metal electrodes at its surface, resulting in local heating of the electrodes and the piezoelectric material behind the electrodes. When the electrode does not cover the surface of the oscillator element in the excitation area, the light beam will not heat the electrode. The absorption in the piezoelectric material itself is small and does not lead to background signals. The reduction of the area covered by the electrodes leads to a slightly reduced electronic signal from the oscillator element, but this effect is largely compensated by the absence of any background signal. Preferably, to prevent absorption on the backside of the interrupted areas when the irradiation has passed the often transparent piezoelectric material, the electrode material is interrupted on the backside as well. Another reason for interrupting the electrode material on the backside is to allow photoacoustic detection by beams passing forward and backward through the cell.

In another embodiment, the electrodes have a high reflection coefficient for light at a wavelength of the light beam. High reflectivity of the incoming light results in low absorption, which results in minimal temperature increase of the oscillator element. For instance when blue light is used for the photo acoustic detection, a metal with a high reflection in this wavelength range can be chosen e.g. silver or aluminum. Gold and brass are less favorable for this wavelength.

The low absorption/ high reflectivity may also be obtained by covering the electrodes with a coating for obtaining the high reflection coefficient. For example, a dielectric layer or dielectric layer stack with appropriate thickness(es) may be used so that a high reflectivity coating is obtained.

Alternatively, the electrodes are, at least in the excitation area, made of a transparent electrically conductive material.

In a preferred embodiment, the piezoelectric material is quartz. Quartz oscillators are well known to be accurate oscillating elements. Preferably, the piezoelectric material is shaped as a tuning fork.

In experiments it has been found that the largest photo acoustic signal and smallest background signals are obtained close to the end of the prongs of the tuning fork. So a preferred embodiment is one wherein the excitation area is situated at an end of two prongs of the tuning fork.

According to a second aspect of the invention a photo acoustic detector is provided comprising an oscillator element according to the invention.

These and other aspects of the invention are apparent from and will be elucidated with reference to the embodiments described hereinafter.

DETAILED DESCRIPTION OF THE INVENTION

Figure 1:
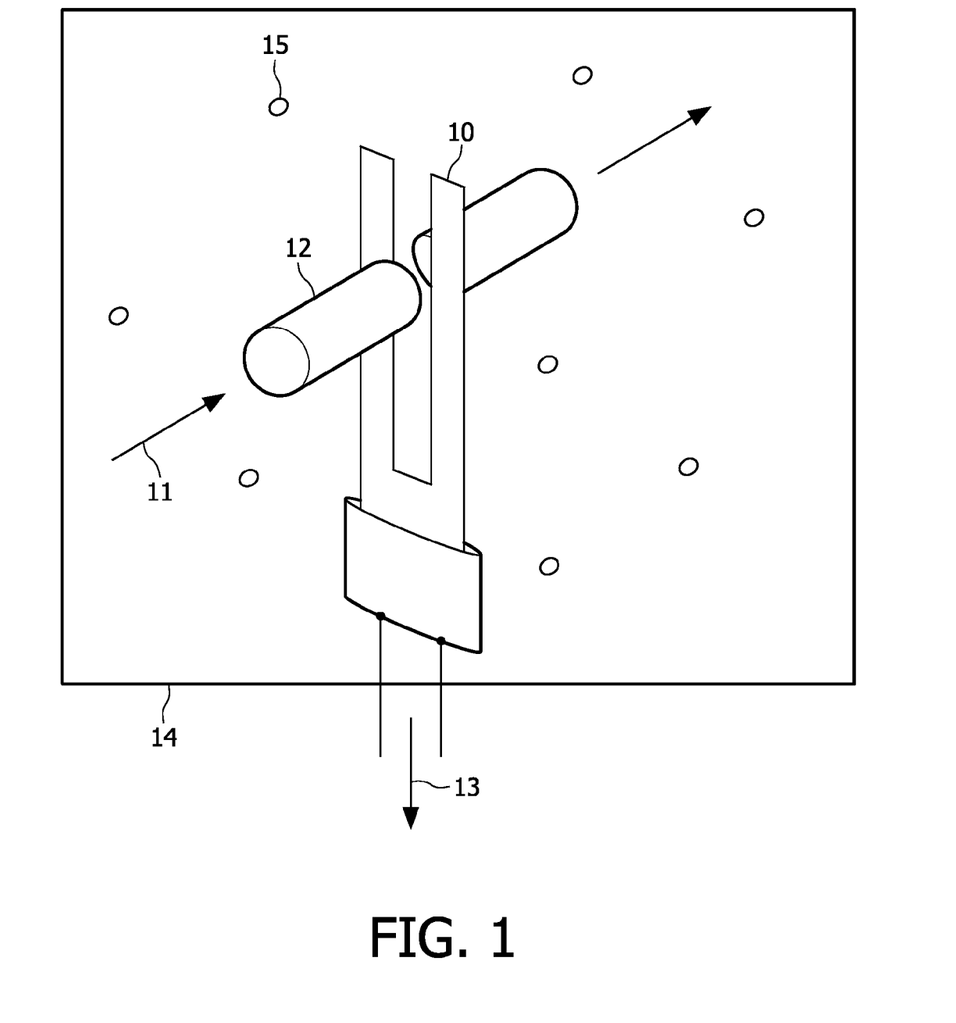
FIG. 1 shows a portion of a photo acoustic trace gas detector.

FIG. 1 shows a portion of a photo acoustic detector. The photo acoustic trace gas detector described hereinafter detects trace gas concentrations in gas mixture, but the invention may also be applied to detect tissue, fluid or solid samples in other sample mixtures. The trace gas detector comprises an oscillator element 10, placed in a gas mixture 14. The gas mixture 14 is contained in a gas cell. In a typical breath analyzing apparatus, the gas cell comprises a gas inlet and a gas outlet for enabling a person to breath air through the gas cell. In this embodiment the oscillator element 10 is a tuning fork, but other shapes of the oscillator element 10 may also be used. A high intensity light beam 11, preferably a laser beam 11, passes through the gas mixture 14 and is focused close to the oscillator element 10. Preferably, the laser beam 11 is focused just between the two prongs of a tuning fork 10. If the light of the laser beam 11 has the correct wavelength, it is absorbed by the molecules of the trace gas 15. The temperature of the gas mixture 14 increases when the excited molecules fall back into their original state. The temperature increase results in a pressure increase. By modulating the amplitude of the light beam 11 at a resonance frequency of the tuning fork 10, the repeated pressure variations cause the tuning fork 10 to resonate. Higher trace gas 15 concentrations result in larger oscillations of the tuning fork 10. In this embodiment, an acoustic cell 12 is provided for amplifying the sound waves and increasing the response of the tuning fork 10. The oscillator signal 13 may be sent to an ADC or other electronic circuit for further processing.

Figure 2:
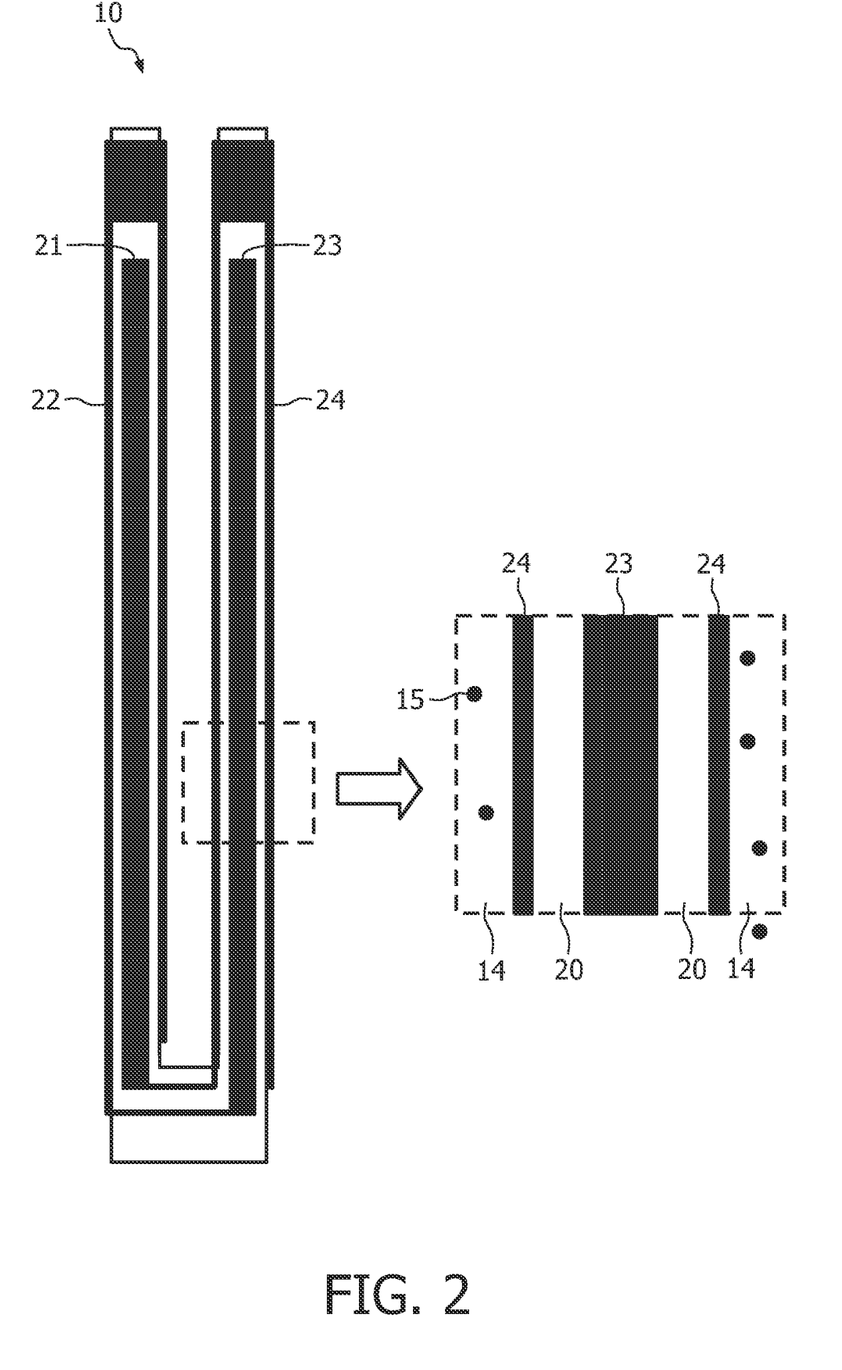
FIG. 2 shows a front view of a prior art oscillator element embodied as a tuning fork.

FIG. 2 shows a front view of a prior art oscillator element embodied as a tuning fork 10. The tuning fork is constituted of a piezoelectric material 20, like quartz, gallium orthophosphate ($GaPO_4$) or lead zirconate titanate ($Pb(ZrTi)O_3$). Piezoelectricity is the ability of crystals to generate a voltage in response to applied mechanical stress. The piezoelectric effect is reversible in that piezoelectric crystals, when subjected to an externally applied voltage, can change shape by a small amount. Electrodes 21-24 on the surface of the piezoelectric material 20 collect the electrical charge originating from the mechanical stress. The electrodes 21-24 are made of a metal to conduct electricity. For the largest electronic response to the resonating of the tuning fork, the electrodes 21-24 cover nearly the whole surface of the piezoelectric material.

Figure 3A:
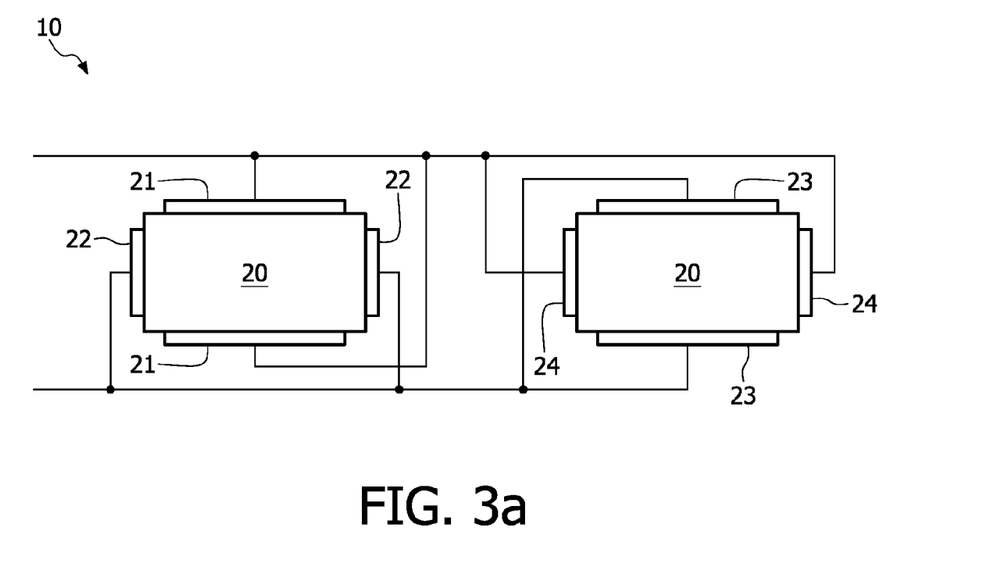
FIGS. 3a and 3b show cross sections of a tuning fork.

In the embodiment shown in FIG. 2, the front and back electrodes 21 of the first prong are connected to the side electrodes 24 of the second prong. The front and back electrodes 23 of the second prong are connected to the side electrodes 22 of the first prong. This electrode configuration is also shown in the cross section of the tuning fork 10 as shown in FIG. 3a.

Figure 3B:
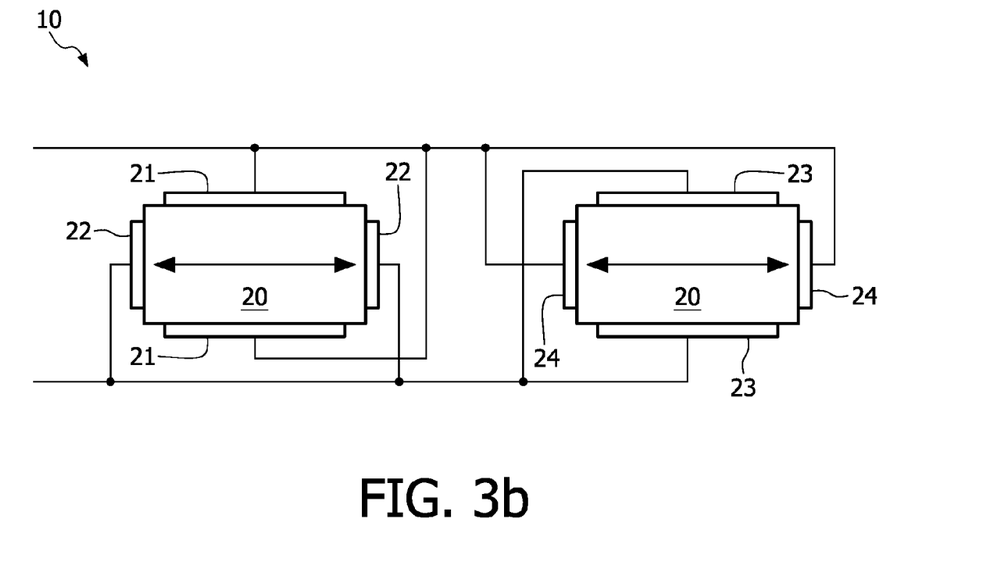

As illustrated in FIG. 3b, this electrode configuration detects and excites movement of the prongs against each other. When one prong is deflected it produces a charge separation that in turn produces a voltage and thus deflects the other prong in the opposite direction. It is an advantage of this electrode configuration that sound waves emanating from a distant source, which sound waves tend to apply a force in the same direction to each of the two prongs, do not excite the tuning fork 10.

Figure 4A:
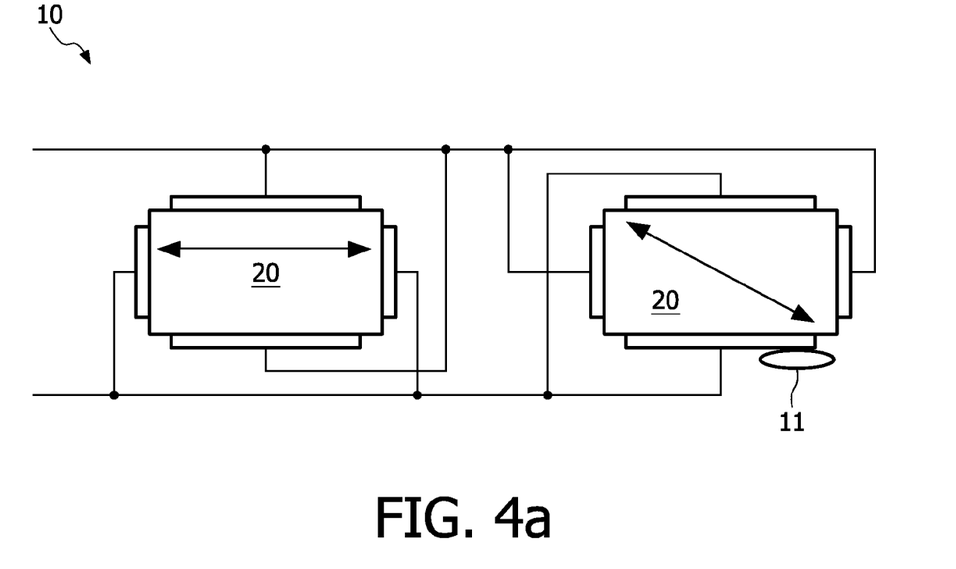
FIGS. 4a and 4b show cross sections of a tuning fork, hit by a light beam.
Figure 4B:
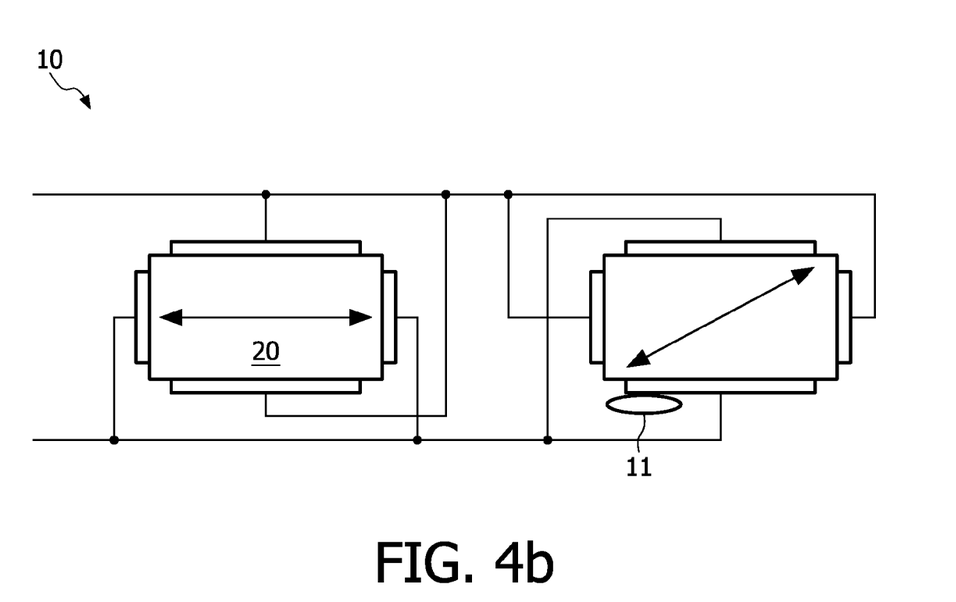

FIGS. 4a and 4b show cross sections of a tuning fork 10, hit by a light beam 11. During photo acoustic trace gas detection a small fraction of the light 11 generally falls on the prongs and in case the light 11 is amplitude modulated at or close to the tuning fork 10 resonance, the tuning fork 10 prongs start to oscillate. The illumination results in a combined sideward and backward-forward oscillation mode. The frequency of this latter oscillation is slightly shifted with respect to the sideward movement. When a fixed frequency is used for amplitude modulation of the light beam 11, this frequency shift is detected as a phase shift in the detected signal 13. These effects interfere with the photo acoustic signal and should preferably be suppressed or circumvented.

Figure 5:
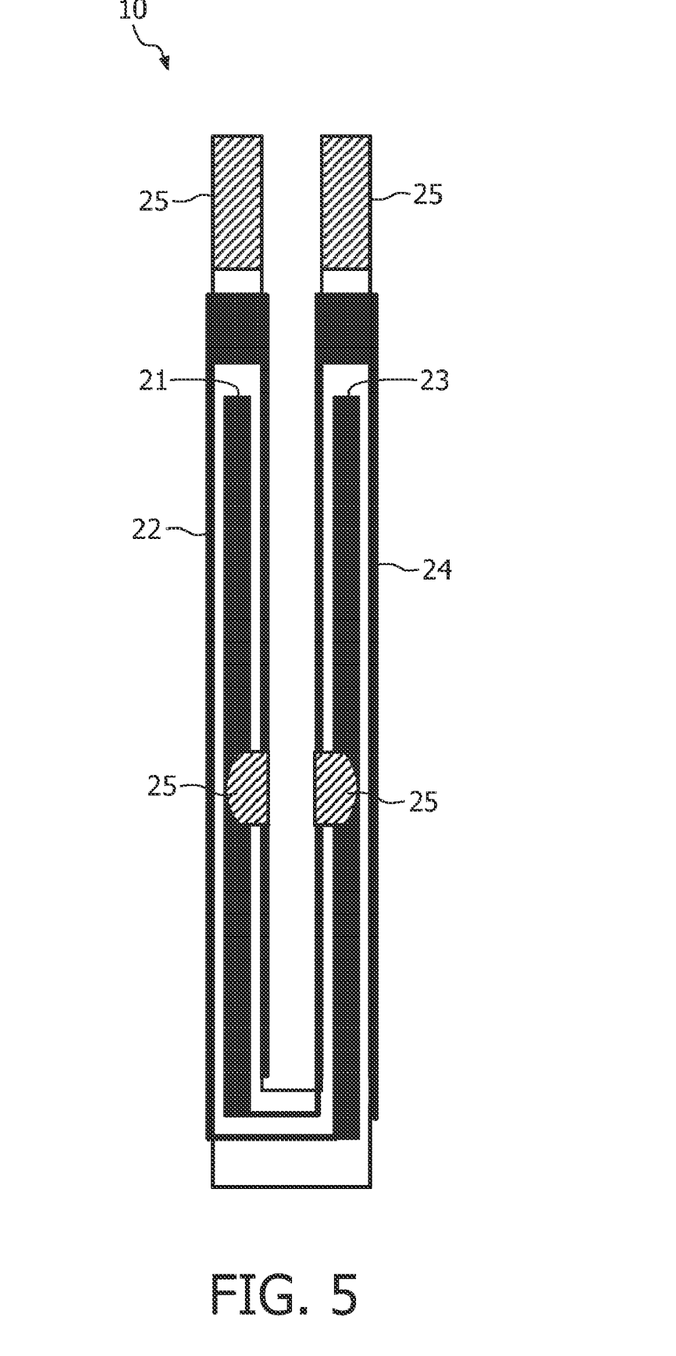
FIG. 5 shows a front view of an oscillator element according to the invention.

FIG. 5 shows a front view of an oscillator element 10 according to the invention. The inventors have observed that that the mechanism lying behind the tuning fork 10 excitation is absorption of the light 11 in the metal electrodes 21-24 at the surface of the tuning fork 10 resulting in a local heating of the electrodes 21-24 and the piezoelectric material 20 behind the electrodes 21-24. The heating results in expansion and mechanical distortion of the piezoelectric material 20, which is picked up electronically via the piezoelectric effect and the electrodes 21-24. By arranging the electrodes 21-24 such a way that heating of the electrodes 21-24 by a light beam 11 is avoided, the sensitivity and the accuracy of the trace gas detection are improved.

In the embodiment shown in FIG. 5 the electrode structures are absent in the areas 25 where the wings of the laser beam 11 fall on the prongs. When the electrode 21-24 does not cover the surface of the tuning fork 10 in the excitation area, the light beam will not heat the electrode 21-24. The absorption in the piezoelectric material 20 itself is negligible and does not lead to background signals. Modification of the electrode will lead to a slightly reduced electronic signal 13 from the oscillating prongs but this effect is largely compensated by the absence of any background signal. The interrupted electrodes can be connected on other parts of the prongs, or the size of the interruption can be chosen in such a way that not the complete electrode is interrupted. To prevent absorption on the backside of the interrupted areas 25 when the irradiation has passed the transparent piezoelectric material 20, the electrode material has to be interrupted on the backside as well. Besides interrupting the electrode it is also possible to use a transparent electrode for instance made of indium tin oxide (ITO).

In experiments it has been found that the largest photo acoustic signal and smallest background signals are obtained close to the end of the prongs. So a preferred embodiment is one where the electrode structures are absent at the end parts of the prongs.

In an alternative embodiment, the material of the electrodes 21-24 is optimized for minimal absorption. For instance when blue light is used for the photo acoustic detection, a metal with a high reflection in this wavelength range can be chosen e.g. silver or aluminum. Gold and brass are less favorable for this wavelength, but may be preferred for other wavelengths. A further reduction can be obtained when the metal is coated with a dielectric layer or dielectric layer stack with appropriate thickness so that a high reflectivity coating is obtained. The coating may be applied to the whole electrodes or only to those parts that are part of or close to the excitation area.

Figure 6:
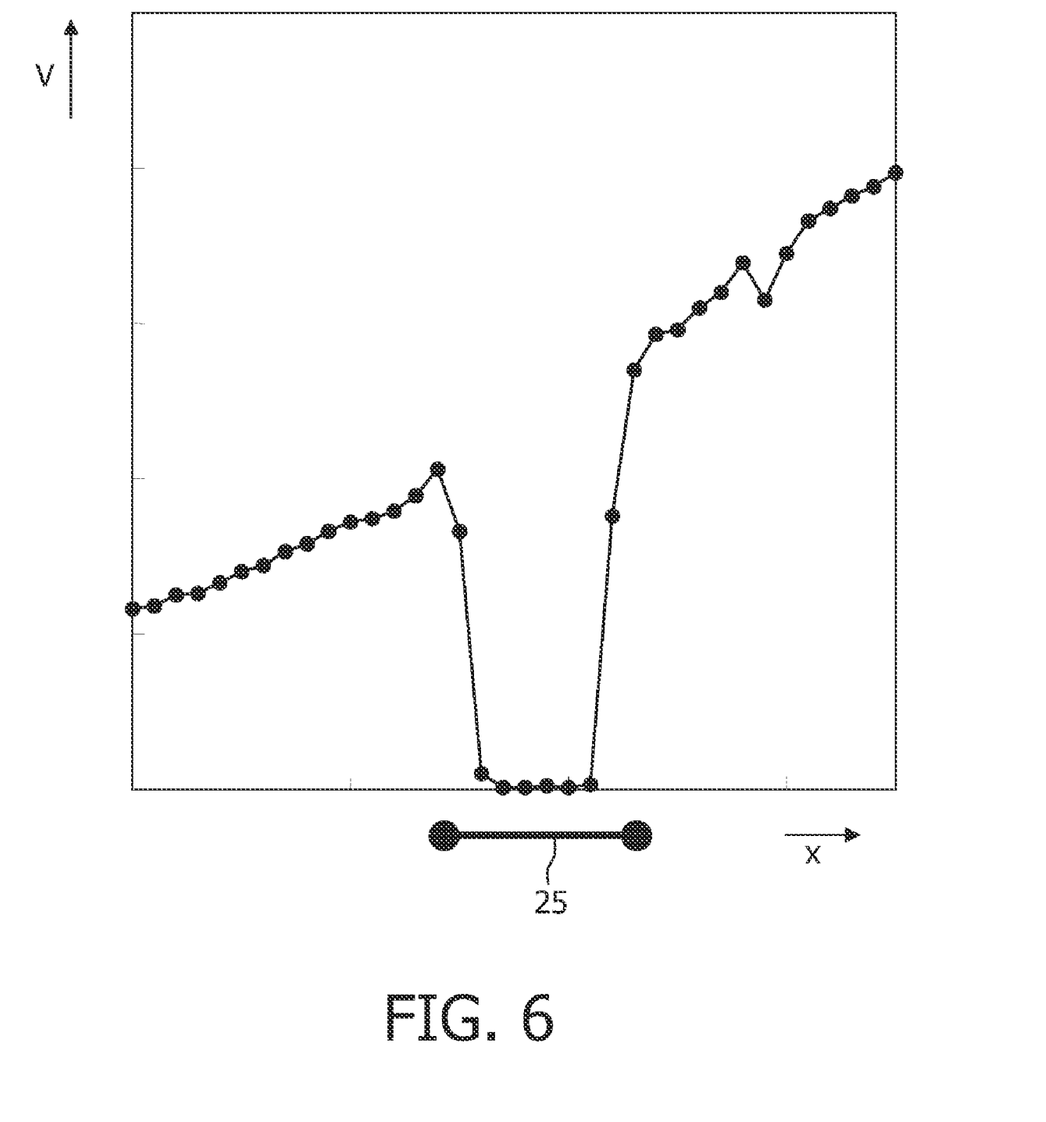
FIG. 6 illustrates the advantage of an oscillator element according to the invention.

FIG. 6 illustrates the advantage of an oscillator element 10 according to the invention. The figure shows the results of an experiment wherein a focused amplitude modulated laser spot was scanned over the tuning fork electrode structure and the corresponding electronic signal 13 was picked-up using a lock-in detection scheme. When the spot is scanned over an area 25 in which the electrode is interrupted, the background signal drops to zero.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the claims enumerating several means, several of these means may be embodied by one and the same item of hardware. The mere fact that certain measures are recited in mutually different dependent claims does not indicate that a combination of these measures cannot be used to advantage.

The invention claimed is:

1. An oscillator element for use in a photo acoustic detector for detecting a concentration of a sample in a sample mixture, the photo acoustic detector using a light beam for excitation of molecules of the sample in proximity of an excitation area of the oscillator element, the excitation resulting in resonance of the oscillator element, the oscillator element comprising:
   piezoelectric material for generating a voltage when mechanically distorted; and
   electrodes at least partially covering a surface of the oscillator element for detecting the generated voltage,
   wherein the excitation area is arranged in such a way that, when the light beam hits the oscillator element, heating of the electrodes in the excitation area by the light beam is avoided by interrupting at least one electrode in the proximity of the excitation area, the at least one electrode having a first portion and a second portion, wherein first portion is heated by absorption of the light beam, and wherein the second portion is substantially transparent to the light beam.

2. The oscillator element according to claim 1, wherein the electrodes do not cover the surface of the oscillator element in the excitation area.

3. The oscillator element according to claim 1, wherein the electrodes have a high reflection coefficient for light at a wavelength of the light beam.

4. The oscillator element according to claim 3, wherein the electrodes are covered by a coating for obtaining the high reflection coefficient.

5. The oscillator element according to claim 1 wherein the electrodes are at least partly made of a transparent, electrically conductive material.

6. The oscillator element according to claim 1, wherein the piezoelectric material is quartz.

7. The oscillator element according to claim 1, wherein the piezoelectric material is shaped as a tuning fork.

8. The oscillator element according to claim 7, wherein the excitation area is situated at an end of two prongs of the tuning fork.

9. A photo acoustic detector comprising the oscillator element as described in claim 1.

10. The oscillator element of claim 1, wherein the first portion of the at least one electrode comprises a metal electrode, and the second portion of the at least one electrode comprises indium tin oxide.

11. The oscillator element of claim 1, wherein the electrodes includes a further electrode having a transparent potion which is substantially transparent to the light beam, the transparent potion being aligned with the second potion of the at least one electrode.

* * * * *